(12) United States Patent
Görnert et al.

(10) Patent No.: US 11,123,211 B2
(45) Date of Patent: Sep. 21, 2021

(54) PIVOTING-LIMITABLE BIAXIAL JOINT

(71) Applicant: BAUERFEIND AG, Zeulenroda-Triebes (DE)

(72) Inventors: Florian Görnert, Zeulenroda-Triebes (DE); Sandro Hebenstreit, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 486 days.

(21) Appl. No.: 15/756,112

(22) PCT Filed: Aug. 15, 2016

(86) PCT No.: PCT/EP2016/069321
§ 371 (c)(1),
(2) Date: Feb. 28, 2018

(87) PCT Pub. No.: WO2017/041993
PCT Pub. Date: Mar. 16, 2017

(65) Prior Publication Data
US 2018/0243119 A1     Aug. 30, 2018

(30) Foreign Application Priority Data
Sep. 9, 2015   (DE) .................... 10 2015 217 205.8

(51) Int. Cl.
*A61F 5/01*     (2006.01)
(52) U.S. Cl.
CPC .... *A61F 5/0123* (2013.01); *A61F 2005/0137* (2013.01); *A61F 2005/0139* (2013.01);
(Continued)

(58) Field of Classification Search
CPC .... A61F 5/0102; A61F 5/0106; A61F 5/0109; A61F 5/0123; A61F 5/0125; A61F 5/013;
(Continued)

(56) References Cited

U.S. PATENT DOCUMENTS

| | | | |
|---|---|---|---|
| 4,732,143 A | 3/1988 | Kausek et al. | |
| 5,038,765 A | * 8/1991 | Young | A61F 5/0123 602/16 |

(Continued)

FOREIGN PATENT DOCUMENTS

| | | |
|---|---|---|
| CN | 201529181 U | 7/2010 |
| CN | 202223393 U | 5/2012 |

(Continued)

OTHER PUBLICATIONS

International Search Report dated Nov. 10, 2016 for corresponding International Application No. PCT/EP2016/069321.
(Continued)

*Primary Examiner* — Rachael E Bredefeld
*Assistant Examiner* — William T Kao
(74) *Attorney, Agent, or Firm* — Pearne & Gordon LLP (57) ABSTRACT

The invention relates to a pivoting-limitable biaxial joint, especially for a joint orthosis for supporting and variably limiting the joint flexion. The invention provides an improvement of known joint orthoses. A limiting wedge (300) can be inserted into the joint housing (200) in the axial direction.

9 Claims, 6 Drawing Sheets

(52) U.S. Cl.
CPC .......... *A61F 2005/0158* (2013.01); *A61F 2005/0165* (2013.01); *A61F 2005/0181* (2013.01)

(58) Field of Classification Search
CPC .......... A61F 5/05841; A61F 5/0585; A61F 5/05858; A61F 2005/0158; A61F 2005/0165; A61F 2005/0167; A61F 2005/0132; A61F 2005/0137; A61F 2005/0139; A61F 2005/0148; A61F 2005/016; Y10T 16/532; Y10T 16/5323; Y10T 16/5361; Y10T 16/551; Y10T 16/5513; Y10T 403/32606; Y10T 403/32951; Y10T 403/32262; Y10T 403/62254; Y10T 403/32557; Y10T 403/32581; Y10T 403/32271; F16B 2/02
See application file for complete search history.

(56) References Cited

U.S. PATENT DOCUMENTS

| | | | |
|---|---|---|---|
| 5,443,444 | A | 8/1995 | Pruyssers |
| 5,662,596 | A | 9/1997 | Young |
| 5,772,618 | A | 6/1998 | Mason et al. |
| 6,402,711 | B1 | 6/2002 | Nauert |
| 7,083,583 | B2 | 8/2006 | Opahle et al. |
| 9,889,036 | B2 | 2/2018 | Chiang et al. |
| 2004/0049140 | A1* | 3/2004 | Doty .......... A61F 5/0123 602/16 |
| 2006/0287624 | A1 | 12/2006 | Popp et al. |
| 2007/0276305 | A1* | 11/2007 | Kahlmeyer .......... A61F 5/0123 602/23 |
| 2008/0082031 | A1 | 4/2008 | Nathanson |
| 2014/0221891 | A1* | 8/2014 | Sreeramagiri .......... A61F 5/0123 602/16 |
| 2017/0340471 | A1* | 11/2017 | Mason .......... A61F 5/0123 |

FOREIGN PATENT DOCUMENTS

| | | |
|---|---|---|
| DE | 102 07 702 C1 | 8/2003 |
| DE | 20 2015 003 755 U1 | 7/2015 |
| WO | 01/10360 A1 | 2/2001 |

OTHER PUBLICATIONS

Witten Opinion dated Nov. 10, 2016 for corresponding International Application No. PCT/EP2016/069321.
Chinese Office Action dated Jul. 11, 2019 for corresponding Chinese Application No. 201680052165.0.
English translation of Written Opinion dated Nov. 10, 2016 for corresponding International Application No. PCT/EP2016/069321.
International Preliminary Report on Patentability dated Mar. 13, 2018 for corresponding International Application No. PCT/EP2016/069321.

* cited by examiner

PIVOTING-LIMITABLE BIAXIAL JOINT

The present invention relates to a pivoting-limitable biaxial joint, especially for a joint orthosis to support and variable limitation of joint flexion. The invention provides an improvement of known joint orthoses.

Medical aids for orthopedics, so-called orthoses, for the maintenance, stabilization or restoration of joint function are known. Mechanically stable orthoses, so-called rigid frame braces are known for the therapeutic mechanical support of the joint function, especially for the controlled guidance of joint movement, in particular for the limitation of the flexion angle of the joint often required in therapy. These attach mechanically to both sides of the joint and bridge the joint with a stiff frame or bridge. The frame construction of the orthosis itself is pivotable at least in the region of the body joint and can thus mechanically support, guide or limit the joint function of the body joint.

It has been found that body joints are not mechanically reproducible by a simple monoaxial hinge function. In order to avoid disadvantageous interfering forces or strains on such joint orthoses, so-called biaxial or multi-axial joints have been developed, which permit an anatomically more correct pivoting of the parts of the joint orthosis in at least two adjacent joint axes. Upper and lower, that is distal and proximal, portions of a joint orthosis are therefore connected by joint rails having a biaxial central joint in a housing. In order to mechanically implement the pivoting of the joint rails in the biaxial joint, the two joint rails which are pivotable in the joint are known to be guided by toothed joint heads which mesh with one another.

In particular for therapeutic measures, it is desirable to limit the pivotal movement of this biaxial joint on the joint orthosis—and thus the flexion and/or extension of the body joint itself—at least temporarily. In the prior art various measures are known, which, however, are either mechanically insufficient or too complex in the operation, so that often the desired function is not achieved due to operating errors. The object of the present invention was to improve a biaxial joint known per se on a joint splint, suitable for use on a joint orthosis, specifically on a rigid frame brace, such that the pivoting angle of this joint can be reliably and at least temporarily limited by simple means. In particular, the pivotal limitation should be easy to use and at the same time be mechanically reliable and robust. In addition, there should be the possibility to implement in a simple way the pivoting limitation at various extends up to the total blockage of the joint function.

To solve the problem the invention provides the subject matter of main claim 1, especially a biaxial joint for a joint orthosis, containing hinged rails, each with toothed joint heads, which are guided in a joint housing between an outer and an inner housing plate and are mounted on joint axes (bearing journals) within the joint housing, the hinge rails being mutually pivotable together intermeshing with each other on their joint heads around the joint axes in the joint housing. According to the invention at least one of the housing plates, in particular at least the outer housing plate, comprises at least one opening in the surface of the housing plate, wherein in each case a limiting wedge can be inserted to the housing in the axial direction. According to the invention, the axially inserted limiting wedge in the inserted state permits the pivoting of the hinge rails in the joint housing to be limited in at least one pivoting direction, since it is provided that the limiting wedge engages with corresponding shoulders of the joint heads starting at a specific pivoting angle of the hinge rails.

It is preferably provided that the limiting wedge extends in the axial direction through the entire joint housing and in particular is guided in both, outer and inner housing plates of the joint housing in a respective opening in a force-fitting, particularly in a positive-locking manner, and in a particular embodiment, exclusively or additionally, by means of friction due to fitting. Accordingly, in a preferred embodiment of the biaxial joint it is provided, that both housing plates each have an opening for receiving and guiding said limiting wedge in the axial direction.

In particular, it is provided that the limiting wedge is formed in one piece and can be subdivided into at least three functional and physical sections. An outer guide shoulder is provided to engage with or in the opening of the outer housing plate, an inner guide shoulder is provided to engage with or in the opening of the inner housing plate. An intermediate central limiting section located therebetween has abutment surfaces on which corresponding shoulders of the joint heads of the hinged rails can stop upon pivoting in order to limit the pivoting of the hinge rails in the joint.

Preferably, the limiting wedge is integrally formed and in particular one-piece. The limiting wedge is preferably made of impact-resistant material, particularly preferably high-strength polymer or metal, preferably selected from aluminum, magnesium, titanium or alloys comprising these. In a particular embodiment, the limiting wedge is formed from an elastically deformable material whose elasticity and temporary deformability enable a damped limitation of the pivoting of the hinged rails. Such an embodiment of the limiting wedge made of elastic material present at least at the region of the central limiting section of the limiting wedge, particularly at least at the region of the stop surfaces of the central limiting section, advantageously enables a physiologically and therapeutically expedient "braking in" into the limitation of the joint movement, which firstly signals the limitation to the wearer early, and, secondly, prevents abrupt onset counter-forces, which can also lead to an overload of the joint as such, which otherwise would be possible. The elastic properties of the limiting wedge or of the relevant sections thereof can be implemented by suitable elastic materials such as elastomers or, alternatively and additionally, by means of spring elements, flat springs, coil springs.

The invention advantageously allows an easily operable and mechanically extremely stable limitation of the pivoting movement of the hinge rails compared to pivot-limited biaxial joints of the prior art. Due to the novel mounting of the at least one limiting wedge in the at least one, preferably in two housing plates, wherein the limiting wedge is extending in the axial direction through the housing, a mechanically particularly stable limitation of the pivotal movement or blockage of the hinge rails on the stops of the limiting wedge is achieved. Since the hinge rails are mounted in their joint heads in joint axes in the axial direction, and the limiting wedge is also inserted in the axial direction and guided in the housing, at the time of pivoting-limitation all lateral forces occurring on the limiting wedge when stopping the joint heads are well and safely received, without the occurrence of resulting force vectors, which would otherwise preclude the secure hold of said limiting wedge in the joint housing. On the contrary, due to the forces actually resulting from the joint stop, the joint wedge is held even more securely in the joint housing due to the form-fitting and frictional connection than in its unloaded state. Advantageously, however, the limiting wedge, especially in the unloaded state, i.e. when not acting to impart pivoting, can be easily and preferably removed from the joint housing without further ado, which facilitates operation.

According to the invention, the limiting wedge is provided with at least one, but especially with two opposing dedicated stop surfaces or stop shoulders, which can come into contact with dedicated shoulders or projections on the joint heads for pivotal adjustment and can thereby stop the pivoting movement. Simple pins, especially with a circular cross-section, which can be inserted into a joint housing and engage there, in particular in holes or oblong holes of the pivoting joint rails or their rod ends, in particular to block the joint movement, are excluded. A limiting wedge according to the invention is not a blocking pin. Without wishing to be bound by theory, it should be noted that such simple blocking pins can block a joint rail as a whole, but in practice they are exposed to high mechanical stresses in the function to limit pivoting out of the movement. In contrast, the construction according to the invention of a specifically shaped limiting wedge provides shoulders and dedicated stop surfaces which, in practical application, even allow a mechanical self-stabilization of the total joint arrangement in the limit case (stop), even if this occurs out of the full motion.

In preferred embodiments, the invention additionally provides that limiting wedges of different dimensions of at least the central limiting section of the limiting wedge are optionally insertable into the joint housing in order to freely select the degree of pivoting-limitation of the joint. In the manner of a modular system, the operator of the joint orthosis can be provided with different and easily replaceable limiting wedges in order to limit the degree of pivoting-limitation in a more or less extend depending on the treatment phase. By that, an easily applicable and mechanically stable adjustment of the pivoting-limitation can be provided. The invention therefore particularly encompasses a joint arrangement for selectively accommodating differently dimensioned limiting wedges for the purpose of selecting or adjusting the pivoting-limitation and also the use of differently dimensioned limiting wedges for the purpose of selecting or adjusting the pivoting-limitation in the joint arrangement according to the invention.

In a preferred embodiment it is also provided that two limiting wedges are inserted into the joint housing to expand the range of applications and therapies of the joint orthosis, whereby the pivotal movement of the joint rail can be limited in both pivoting directions. For this purpose, it is particularly provided that at least one of the housing plates of the joint housing has at least two preferably opposite openings, into each of which a limiting wedge can be inserted in the axial direction. Also in this case, both limiting wedges can simply be inserted from the same side into the housing. Operation and mechanical action of a joint with two insertable limiting wedges do not differ from the embodiment described herein with one limiting wedge. The advantages and effects described herein for a version with a limiting wedge accordingly apply accordingly to the preferred embodiment with two limiting wedges. The arrangement of the limiting wedges for limiting the pivotal movement of the hinge rails in both pivoting directions is readily apparent to those skilled in the art with the knowledge of the embodiment described herein with a single usable limiting wedge. Preferably, a second opening is provided for this purpose in the at least one housing plate, which is the first opening of the housing plate for receiving the first limiting wedge in the sectional plane through the joint, which lies substantially in the bisector of the pivoting angle of the hinge rails and parallel to the pivot axes and preferably in the pivot axes, mirrored opposite.

In a particular embodiment, at least one cover is additionally provided by means of which the joint housing can be covered. Preferably, exclusively or at least, the joint housing on the outer side, on the outer housing plate, i.e. in the applied state of the joint orthosis on the side facing away from the body, is covered with this cover. In this case, it is particularly provided that the cover can engage on the housing via at least one locking latch or a comparable closure element with a mating counter-closure element formed in the housing, preferably in the housing cover, preferably in a form-fitting manner in order to hold the cover onto the housing. Advantageously, the cover covers the housing plate at least in the region of the opening for receiving the limiting wedge in the housing such that a limiting wedge inserted there cannot disengage from the housing. By means of this simple way one or more limiting wedges can be held securely in the joint housing. Preferably, no further measures for securing the one or more limiting wedges in the joint housing are required. In a preferred embodiment of this cover, it has at least one latching element, preferably a latching lug, which is specifically designed to hold the at least one limiting wedge on the cover, so that the limiting wedge together with the cover controllably used in the at least one opening in the housing plate or removable. This embodiment particularly advantageously allows that the limiting wedge can be easily removed from the joint or used together with the cover, especially when the joint orthosis is already worn on the body. Particularly in connection with differently dimensioned limiting wedges for the exact adjustment of the degree of pivoting-limitation, in practical application the appropriate limiting wedge can be selected in a simple manner from a "modular system", inserted into the cover according to the invention, which preferably engages there on a latch and is thus held on the cover, and then be inserted directly in the joint housing. Alternatively, the limiting wedge can also be placed directly in the joint housing and then the cover can be placed, which preferably protects the limiting wedge against disengagement or falling out of the opening and holds it in place in the joint housing. In this case, it is preferably provided that, when the cover is placed, the latching lug, which is preferably provided on the cover, also engages the limiting wedge already inserted into the joint housing and connects it to the lid. In this case, it is also easy to remove the axially inserted limiter wedge from the joint housing, especially by removing this cover. In these embodiments, the joint cover thus serves as a tool for the simple and controlled insertion and removal of the limiting wedge. Advantageously, all of these measures for inserting or exchanging the limiting wedges can also be easily performed on a joint orthosis already attached to the patient, so that easier and safer handling is possible.

Furthermore, in the region of the insertable limiting wedge in a preferred embodiment the cover has at least one window, as a result of which a limiting wedge remains visible even in the state mounted on the joint housing. A number embossed in the limiting wedge, especially a grading and/or other marking, especially a color marking, is visible from the outside and serves to identify the limiting wedge currently being used. In this case too, the axial insertion direction of the limiting wedge according to the invention is advantageous in the practical application since the marking can also be read easily when the orthosis is viewed from the side.

The invention also provides a joint orthosis, comprising at least one biaxial joint, wherein according to the invention at least one limiting wedge can be inserted to in the axial direction. A particular subject of the invention is a knee joint orthosis with at least one, preferably two, of these biaxial joints according to the invention.

Finally, the invention also relates to the use of at least one limiting wedge insertable in the axial direction in a joint housing for limiting the pivoting angle of joint rails in a biaxial joint, as described herein.

The invention will be further described by the following specific embodiments and figures not to be understood to be limiting to its scope.

Figure 1:
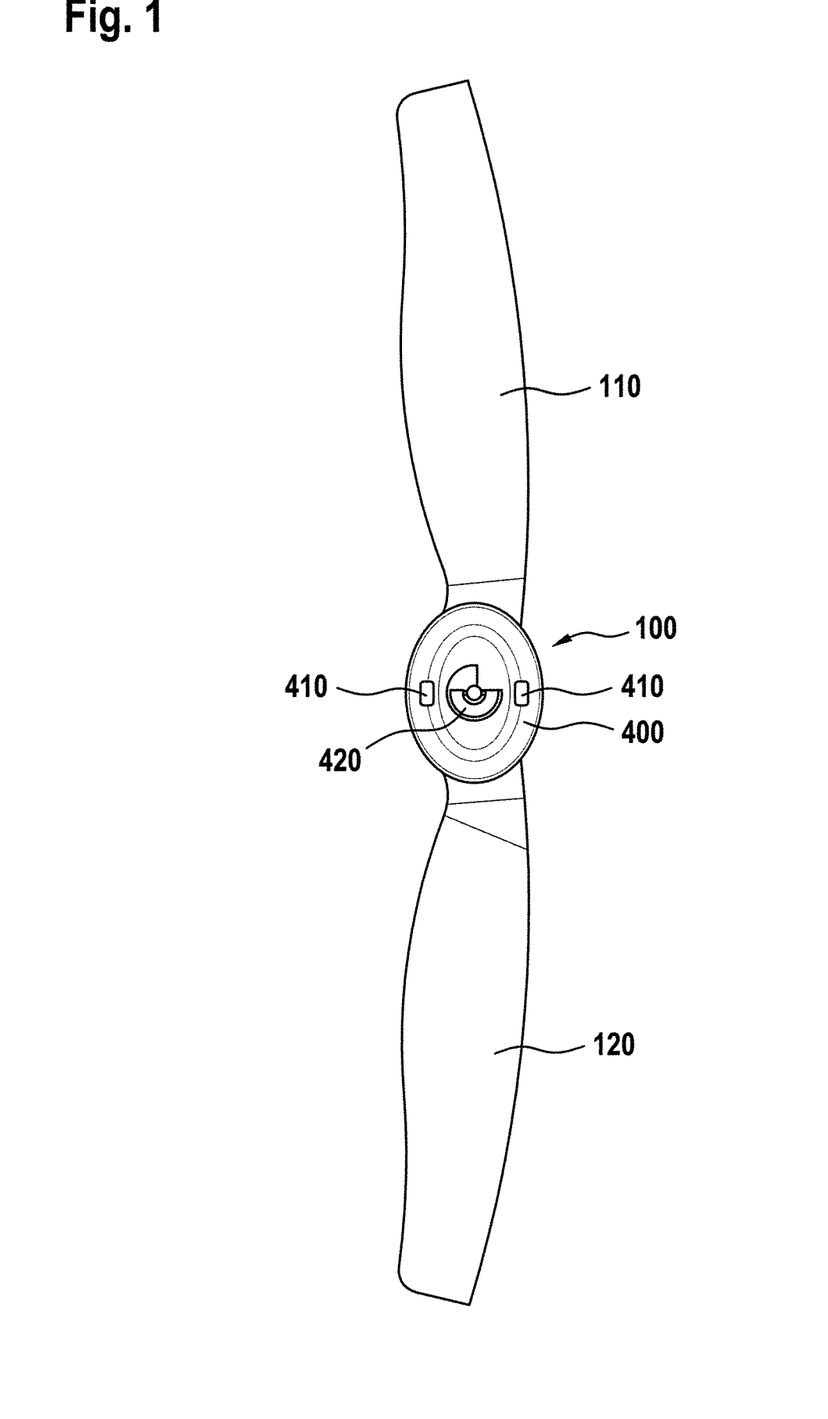

FIG. 1 shows a schematic general view in plan view of one embodiment of the joint splint according to the invention for use in a joint orthosis, particularly in a rigid frame brace for the knee. From the joint 100 extend the two arm-shaped hinge rails 110, 120 articulated therein. As depicted here, in the applied state of the rigid frame brace the joint housing 200 (not visible) is completely covered by a cover 400 at least on the side of the joint housing opposite to the body joint. In the embodiment illustrated here, the cover 400 has at least one window 410. The cover 400 is held in place by a central locking latch 420 on a mating counter-locking element 246 (not shown) formed in the housing.

Figure 2:
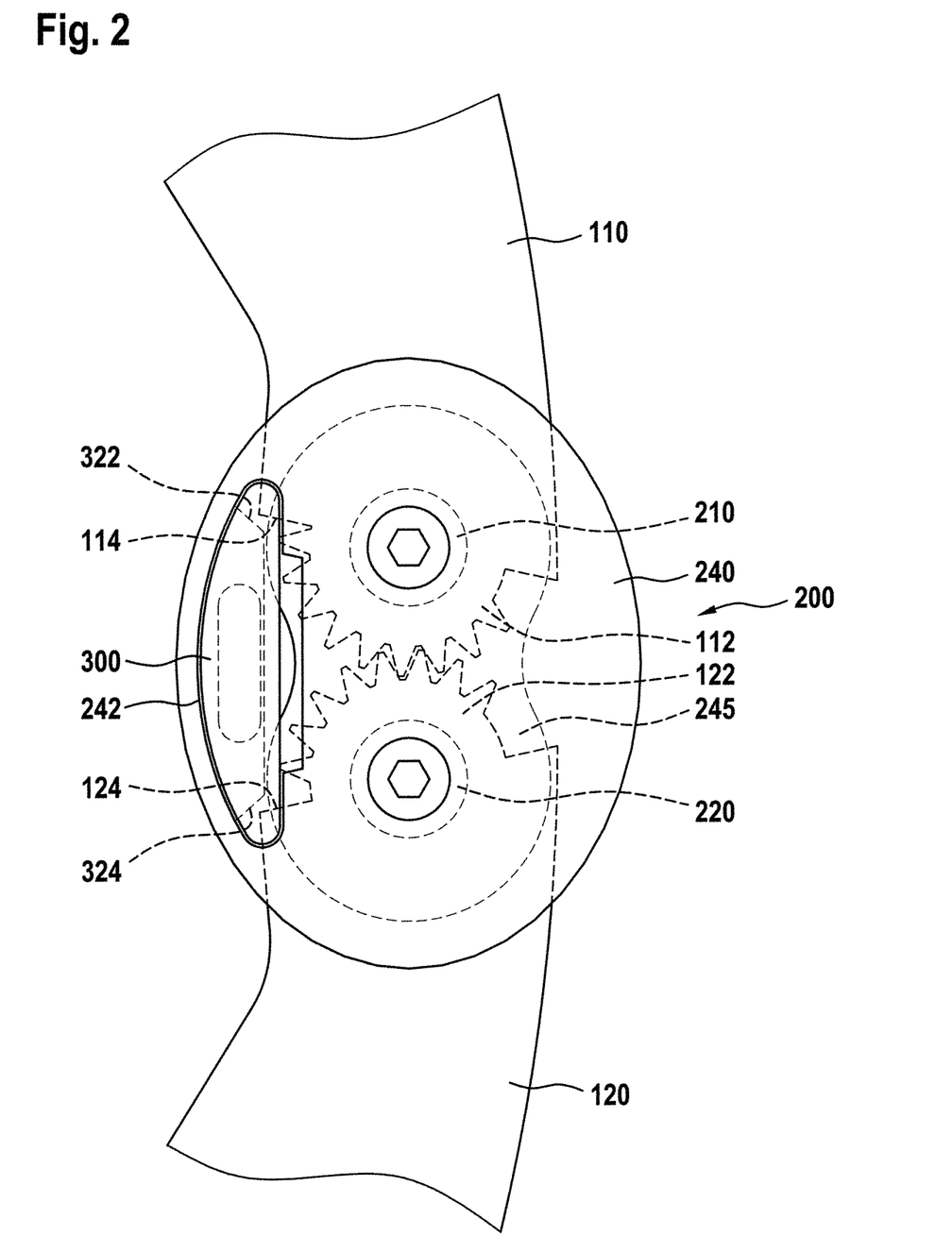

FIG. 2 shows a schematic detail view in plan view of one embodiment of the invention of the joint housing 200 with cover 400 and limiting wedge 300. The hinge rails 110, 120 are each rotatably mounted in joint axes 210, 220 and guided between two housing plates 240, 250. Only the outer housing plate 240 is depicted here, The joint axes 210, 220 are expediently screwed or otherwise firmly connected to both housing plates 240, 250 spacing the two housing plates 240, 250 from one another. Optionally, sliding plates 245, 255 are provided between the housing plates and the hinge rails. The figure depicts the outer slide plate 245 between hinge rails 110, 120 and the outer housing plate 240. When pivoting, the joint heads 112, 122 of the hinge rails intermesh in a toothing. Shoulders 114, 124 are formed at each joint head 112, 122, at least on one side following the respective toothed sprocket. At least on this side of the joint, at least in one of the housing plates 240, 250 of the joint body 200, preferably at least in the outer housing plate 240, a recess or opening 242 is formed which serves to accommodate a limiting wedge 300 insertable in the axial direction. In a preferred embodiment, an opening 252 is additionally provided in the inner housing plate 250, which can engage with a shoulder of the same limiting wedge 300 in order to safely guide the limiting wedge on both sides in the joint housing 200. When pivoting the hinge rails 110, 120, respective shoulders 114, 124 come into contact with stop surfaces 322, 324 of the limiting wedge at a determined pivot angle and thus limit the further pivoting of the hinge rails 110, 120. Depending on the dimensioning of the limiting wedge 300, in particular of the spacing of the stop surfaces 322, 324 from each other, the pivot angle of the hinge rails 110, 120 in the joint 100 is more or less limited. In a variant, corresponding shoulders 114, 124 are additionally formed on the opposite side of the respective joint heads 112, 122. The cover 400 can be fixed via a central locking latch 420 to a mating counter-locking element 246 formed in the joint housing 200.

Figure 3A:
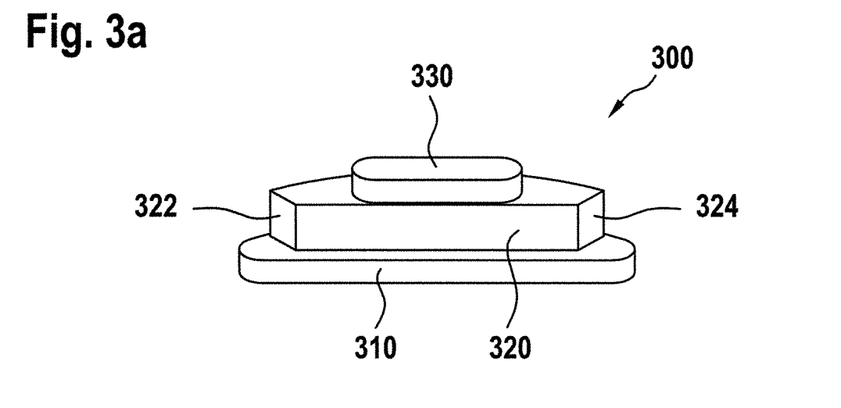
Figure 3B:
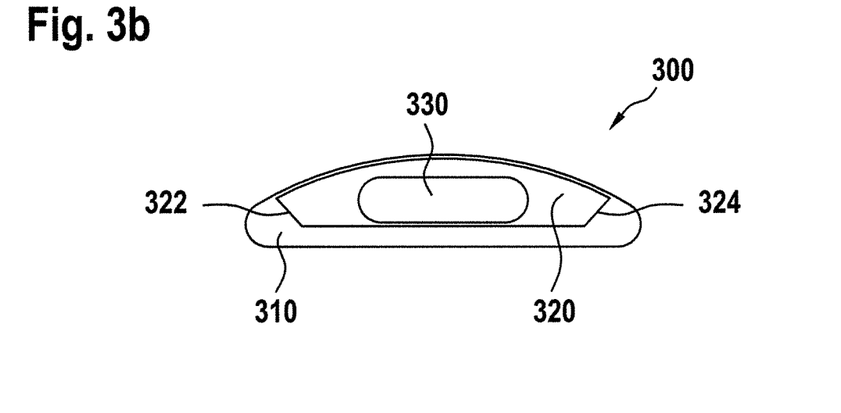
Figure 3C:
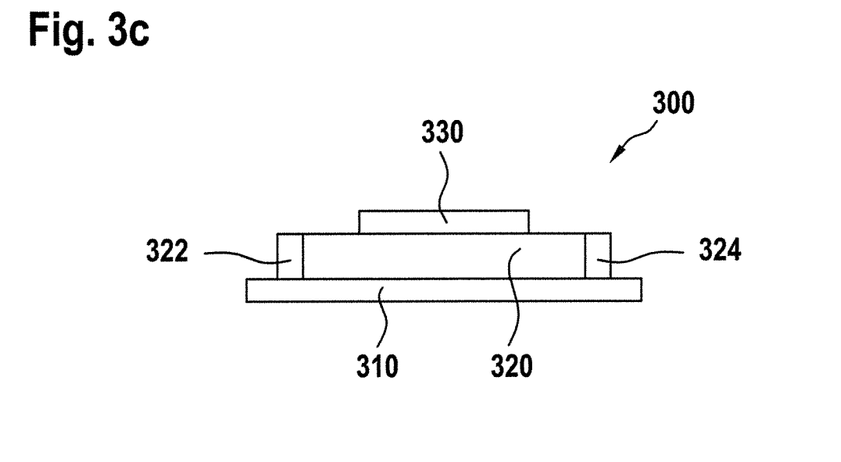

FIGS. 3a, 3b, 3c show views of a limiting wedge, which according to the invention can be inserted into the joint housing. The wedge is divided into at least three functional sections. An outer guide shoulder 310 is particularly adapted to engage the aperture 242 of the outer housing plate 240. An inner guide shoulder 330 is particularly adapted to engage the aperture 252 of the inner housing plate 250. The intermediate central portion 320 serves the functional limitation of the pivoting movement. For this purpose, this central limiting section 320 comprises stop surfaces 322, 324 which, in the inserted state, can come into contact with the shoulders 114, 124 respectively formed on the joint heads 112, 122. FIGS. 3a, 3b, 3c show an embodiment of the limiting wedge 300, which is particularly suitable for insertion in the axial direction according to the invention. Other embodiments and variants thereof, which allow axial insertion, especially from the side of the outer housing plate 240, and ensure a tight fit of the limiting wedge 300 in the joint housing 200, are also conceivable and subject of this invention.

Figure 4:
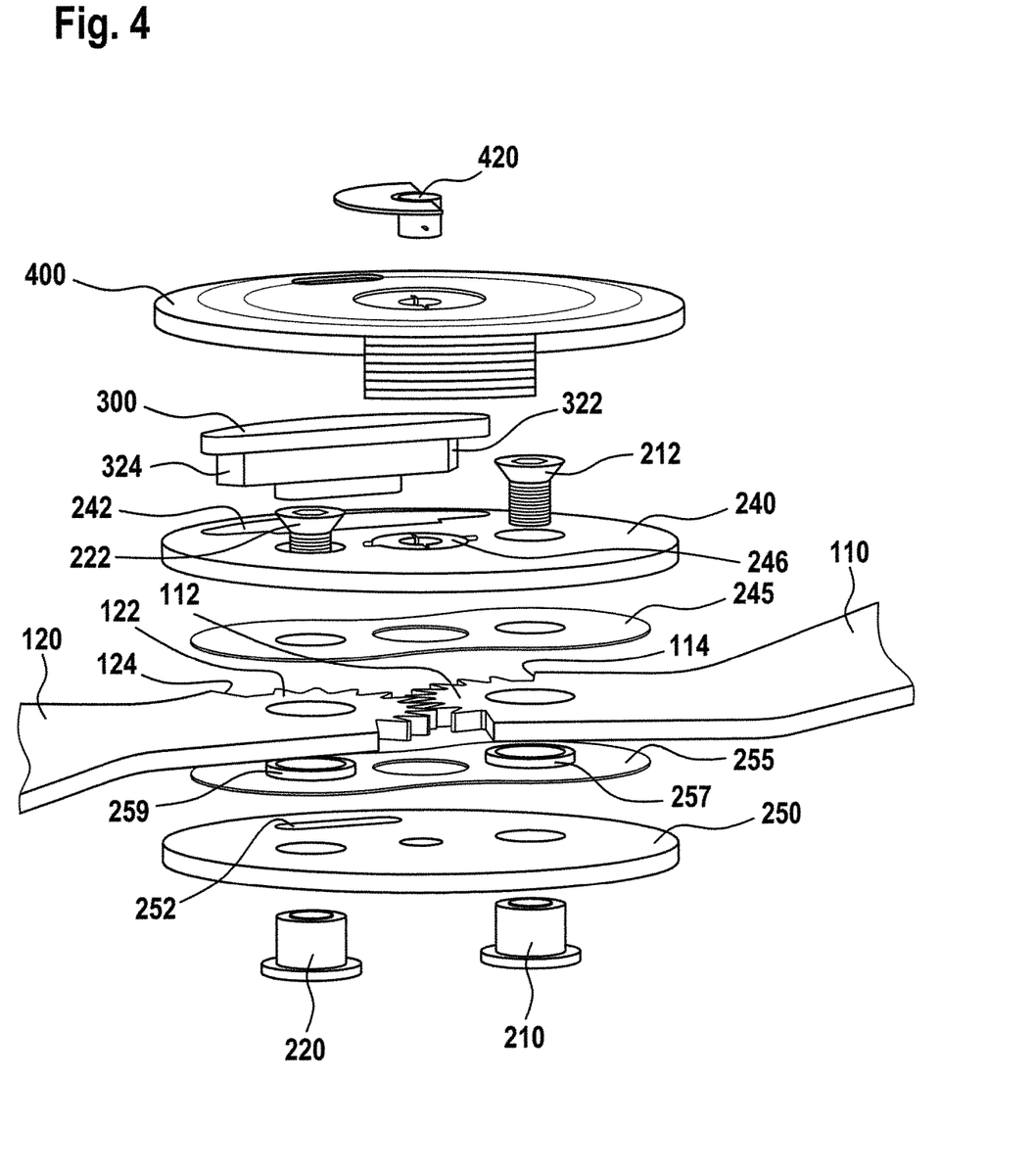

FIG. 4 shows a specific variant of the embodiment according to FIG. 2 of the joint according to the invention in detail in a perspective exploded view. The two housing plates 240, 250 are bolted together in this embodiment by means of the two joint axes 210, 220 via screws 212, 222 and spaced from each other. The hinge rails 110, 120 are pivotally mounted on the joint axes 210, 220, respectively. In particular, slide plates 245, 255 each have bearing shoulders 257, 259, which each form a slide bearing sleeve between the joint axes 210, 220 and the respective bearing bush of the hinge rails 110, 120.

Figure 5:
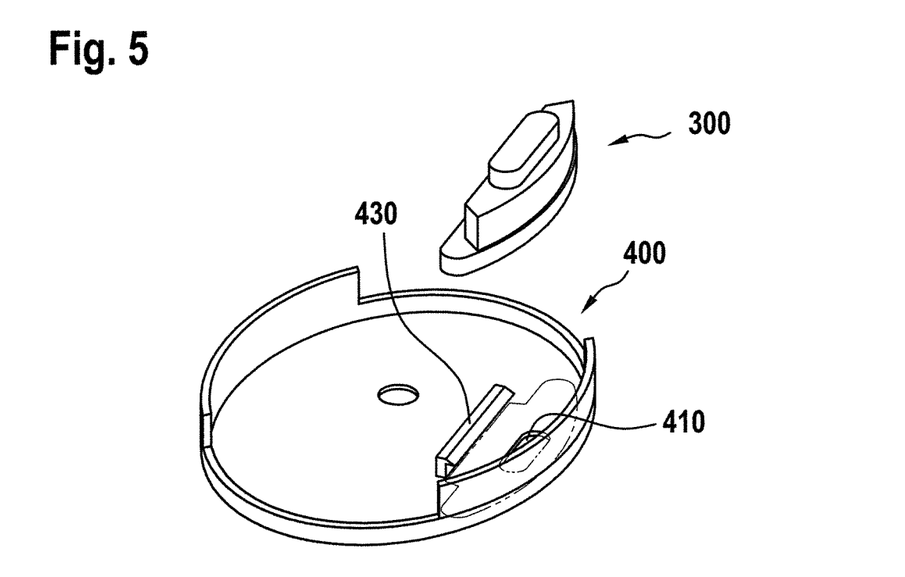

FIG. 5 shows a perspective view of the cover 400 and the limiting wedge 300. In a preferred embodiment, the limiting wedge 300 can be inserted into the cover 400 and is held in place by at least one latching element 430 formed on the cover. In this embodiment, the limiting wedge 300, together with the cover 400, can be inserted and removed as an integral unit into the joint housing 200 in the manner according to the invention. For this purpose, at least the opening 242 of the outer housing plate 240 may have at least one additional recess 243 for receiving the latch 430 of the cover 400 in the assembled state. The at least one recess 243 in the opening 242 of the outer housing plate can also serve to code the limiting wedges which can be used there, in order to limit the choice in use. The deployable limiting wedges selectively comprise at the outer guide shoulder 310 additional bulges or lugs, which correspond to the recess 243 according to the key-lock principle. By means of the window 410 in the cover, a print or an engraving present on the outer surface of the limiting wedge 300, in particular in the outer guide shoulder 310, can also be recognized in the assembled state of the hinge, and thus the type of limiting wedge used in each case can be displayed.

Figure 6:
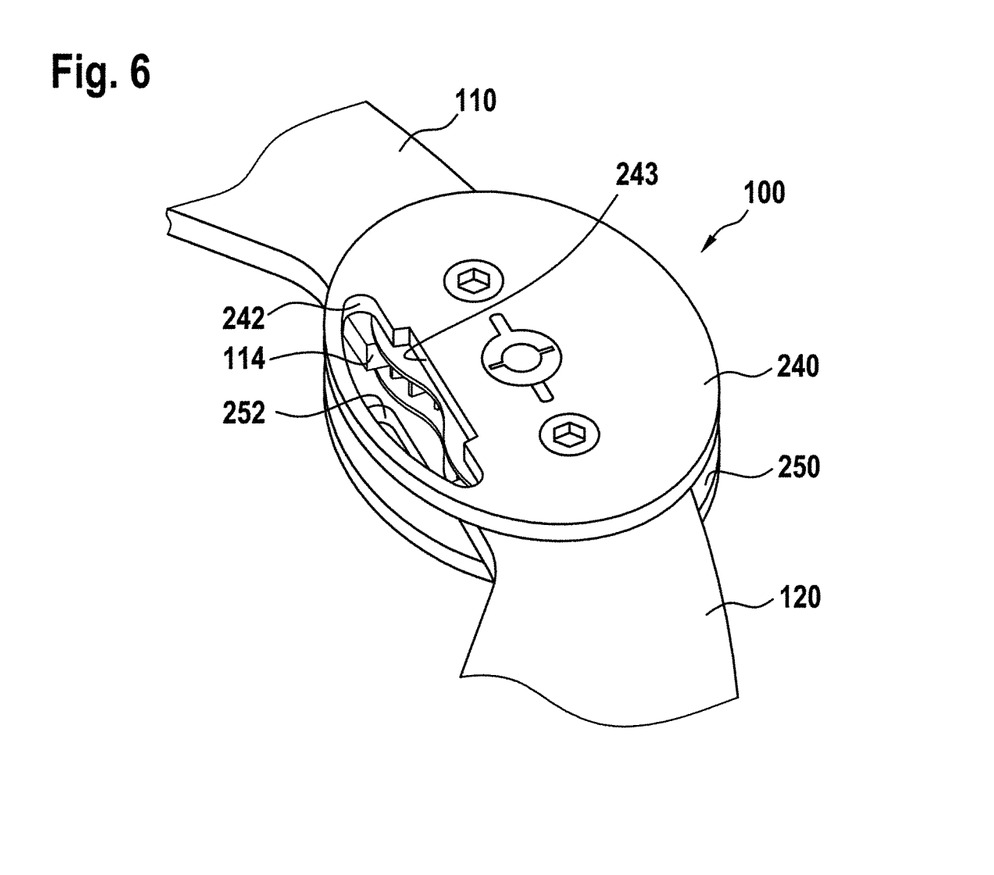

FIG. 6 shows a perspective view of the joint 100 according to FIGS. 2 and 3 with corresponding recesses 242, 243 at least in the outer housing plate for receiving the cover 400 with limiting wedge 300 according to FIG. 5.

Figure 7:
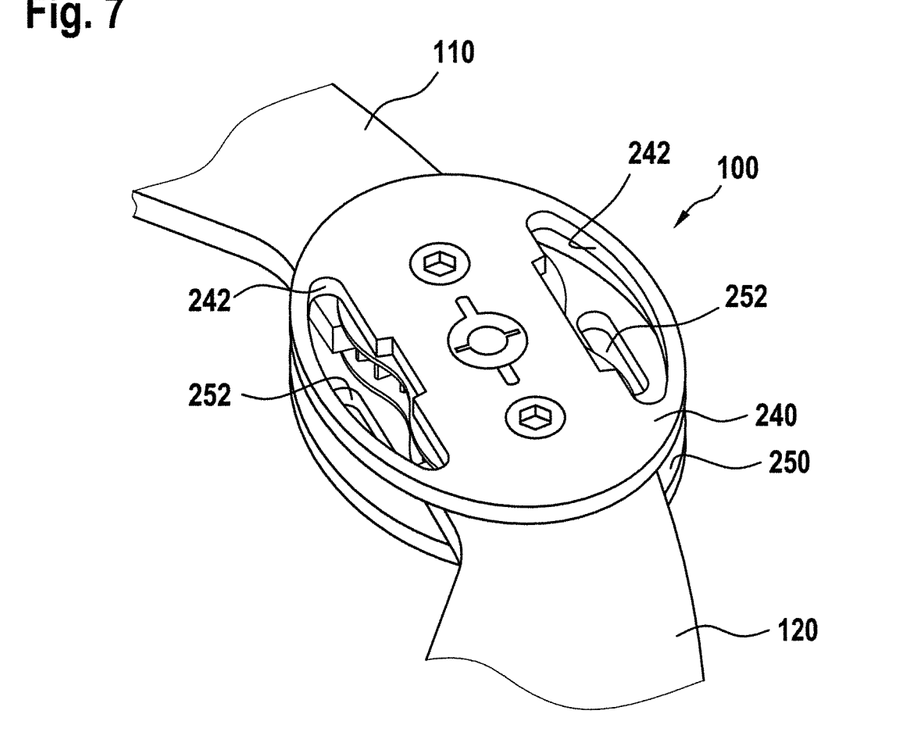

FIG. 7 shows a perspective view of a variant of the joint 100 according to FIGS. 2, 3 and 6, on both sides of the hinge rails 110, 120 perforations 242, 252 for receiving limiting wedges 300 on opposite sides being formed in the joint housing 200 in order to provide the pivoting of the hinge rails 110, 120 in the joint housing 200 to suitably limit both pivot directions.

Figure 8:
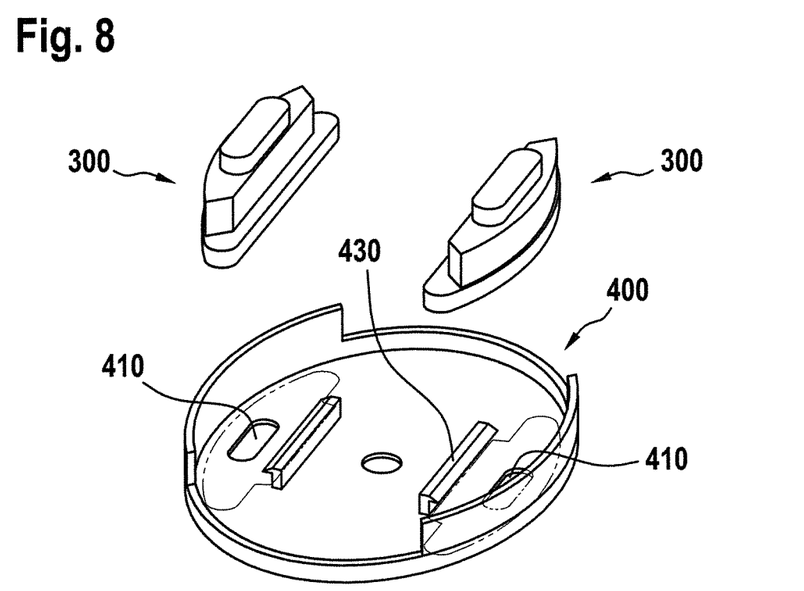

FIG. 8 shows a perspective view of a cover 400 and limiting wedges 300, specifically suitable for the variant shown in FIG. 7, with two opposing recesses 242 for receiving two limiting wedges 300. In particular, the limiting wedges 300 can each be inserted into the cover 400 and are preferably held in place by at least one latching element 430 formed on the cover 400. Through the windows 410 in the cover an existing imprint or engraving, in each case one on the outer surface of the limiting wedge 300, especially in the outer guide shoulder 310, can be recognized even in the assembled state of the joint and thus the type used each limiting wedge be displayed.

The invention claimed is:

1. A biaxial joint for a joint orthosis, comprising:
   hinge rails each having toothed joint heads, the joint heads being guided in a joint housing between outer and inner housing plates thereof, and being rotatably mounted in joint axes within the joint housing in a radial direction, the hinge rails being rotatable together about the joint axes with their toothed joint heads intermeshing with each other,
   wherein both of the housing plates comprise at least one opening for receiving and guiding a one-piece limiting wedge in an axial direction, perpendicular to the radial direction, wherein the at least one opening of one of the housing plate is configured such that the one-piece limiting wedge is insertable from an outside of the joint housing and into the joint housing, in the axial direction, after the joint housing has been assembled, wherein the one-piece limiting wedge in the inserted state can engage at a determined rotation angle with corresponding shoulders on the joint heads of the hinge rails to limit rotation of the hinge rails in at least one pivoting direction,
   wherein the one-piece limiting wedge comprises at least three functional sections:
      an outer guiding shoulder engageable with the opening of the outer housing plate;
      an inner guiding shoulder engageable with the opening of the inner housing plate; and
      an intermediate central limiting portion having stop surfaces.

2. The joint according to claim 1, wherein the joint housing is coverable with at least one cover, the cover on the housing being engageable via a locking latch with a mating locking element formed within the housing to hold the cover to the housing.

3. The joint according to claim 1, wherein the cover has at least one latching element specifically designed to hold the limiting wedge at the cover so that the limiting wedge together with the cover is controllably insertable or removable at the at least one opening of the housing plates.

4. The joint according to claim 1, wherein a sliding plate is inserted between each housing plate and the hinge rails.

5. The joint according to claim 1, wherein in at least one housing plate two opposite openings are formed, for separately receiving in each case a limiting wedge to limit rotation of the hinge rails in both pivoting directions.

6. A joint orthosis, comprising at least one biaxial joint according to claim 1.

7. A knee orthosis comprising the biaxial joint of claim 1.

8. The joint according to claim 1, wherein the one-piece limiting wedge extends in the axial direction through an entirety of the joint housing.

9. The joint according to claim 8, wherein the joint housing is coverable with at least one cover.

* * * * *